(12) United States Patent
Doucet et al.

(10) Patent No.: US 11,439,498 B2
(45) Date of Patent: *Sep. 13, 2022

(54) PROSTHESIS FOR SUPPORTING A BREAST STRUCTURE

(71) Applicant: Sofradim Production, Trévoux (FR)

(72) Inventors: Genevieve Doucet, Villefranche sur Saône (FR); Thierry Brune, Jarnioux (FR); Xavier Couderc, Frans (FR); Cecile Beausseron-Valentin, Lyons (FR)

(73) Assignee: SOFRADIM PRODUCTION, Trevoux (FR)

( * ) Notice: Subject to any disclaimer, the term of this patent is extended or adjusted under 35 U.S.C. 154(b) by 182 days.

This patent is subject to a terminal disclaimer.

(21) Appl. No.: 16/850,063

(22) Filed: Apr. 16, 2020

(65) Prior Publication Data

US 2020/0237500 A1 Jul. 30, 2020

Related U.S. Application Data

(62) Division of application No. 15/920,597, filed on Mar. 14, 2018, now Pat. No. 10,660,741, which is a
(Continued)

(30) Foreign Application Priority Data

Apr. 24, 2015 (EP) ..................................... 15305634

(51) Int. Cl.
*A61F 2/12* (2006.01)
*A61F 2/00* (2006.01)

(52) U.S. Cl.
CPC .............. *A61F 2/12* (2013.01); *A61F 2/0063* (2013.01); *A61F 2250/0018* (2013.01);
(Continued)

(58) Field of Classification Search
CPC .. A61F 2/12; A61F 2/0063; A61F 2250/0018; A61F 2250/0021; A61F 2250/0028; A61F 2250/0063
(Continued)

(56) References Cited

U.S. PATENT DOCUMENTS 1,187,158 A 6/1916 Mcginley
3,054,406 A 9/1962 Usher
(Continued)

FOREIGN PATENT DOCUMENTS

CA 1317836 C 5/1993
CN 201879864 U 6/2011
(Continued)

OTHER PUBLICATIONS

Amid, P., "Lichtenstein tension-free hernioplasty: Its inception, evolution, and principles," Hernia, 2004; pp. 1-7, 8, published online Sep. 2003.
(Continued)

*Primary Examiner* — Suzette J Gherbi
(74) *Attorney, Agent, or Firm* — Weber Rosselli & Cannon LLP

(57) ABSTRACT

The invention relates to a prosthesis for supporting a breast implant comprising:
a reinforcement part configured to receive a curved lower portion of a breast implant, the reinforcement part having an elongation under 50N in the vertical direction of E1,
a fixation part intended to be fixed to the pectoral muscle, the fixation part having an elongation under 50N in the vertical direction of E2, and
a transition part connecting together the reinforcement part and the fixation part, said transition part having an elongation under 50N in the vertical direction of E3,
(Continued)

wherein E3 is greater than E1 and greater than E2.

20 Claims, 5 Drawing Sheets

Related U.S. Application Data division of application No. 15/099,633, filed on Apr. 15, 2016, now Pat. No. 9,931,198.

(52) U.S. Cl.
CPC ............... *A61F 2250/0021* (2013.01); *A61F 2250/0028* (2013.01); *A61F 2250/0063* (2013.01)

(58) Field of Classification Search
USPC ........................................................ 623/7–8
See application file for complete search history.

(56) References Cited

U.S. PATENT DOCUMENTS

| | | |
|---|---|---|
| 3,118,294 A | 1/1964 | Van Laethem |
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,570,482 A | 3/1971 | Shigeru et al. |
| 3,718,725 A | 2/1973 | Hamano |
| 4,006,747 A | 2/1977 | Kronenthal et al. |
| 4,060,081 A | 11/1977 | Vannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schaefer |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,840,629 A | 6/1989 | Bustos |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,071,433 A | 12/1991 | Naestoft et al. |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,368,602 A | 11/1994 | Torre |
| 5,370,650 A | 12/1994 | Jonathan et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,584,884 A | 12/1996 | Pignataro |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |

(56) References Cited

U.S. PATENT DOCUMENTS

| | | |
|---|---|---|
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D Aversa et al. |
| 6,113,623 A | 9/2000 | Sgro |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Robert |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Mueller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,666,893 B2 * | 12/2003 | Burg .................. A61F 2/0063 623/23.64 |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Bryan et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | Devore et al. |
| 6,746,458 B1 | 6/2004 | Cloud |

(56) References Cited

U.S. PATENT DOCUMENTS

| | | |
|---|---|---|
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Dry et al. |
| 7,393,319 B2 | 7/2008 | Merade et al. |
| 7,476,249 B2 | 1/2009 | Frank |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,372 B2 | 3/2010 | Shfaram et al. |
| 7,670,380 B2 | 3/2010 | Cauthen, III et al. |
| 7,682,381 B2 | 3/2010 | Rakos et al. |
| 7,709,017 B2 | 5/2010 | Tayot et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,875,074 B2 * | 1/2011 | Chen ................... A61F 2/12 623/8 |
| 7,900,484 B2 | 3/2011 | Cherok et al. |
| 7,931,695 B2 | 4/2011 | Ringeisen |
| 7,998,152 B2 | 8/2011 | Frank |
| 8,007,531 B2 | 8/2011 | Frank |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,506,627 B2 | 8/2013 | Van et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,728,159 B2 | 5/2014 | Kim et al. |
| 8,734,471 B2 | 5/2014 | Deitch |
| 8,746,014 B2 | 6/2014 | Mortarino |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 9,931,198 B2 * | 4/2018 | Doucet ................... A61F 2/12 |
| 10,398,542 B2 * | 9/2019 | Griffin ................... A61F 2/12 |
| 10,660,741 B2 * | 5/2020 | Doucet ................... A61F 2/12 |
| 2002/0087174 A1 | 7/2002 | Capello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0036266 A1 | 2/2006 | Sulamanidze et al. |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | Mcalexander et al. |
| 2007/0129736 A1 | 6/2007 | Solecki |
| 2007/0198040 A1 | 8/2007 | Buevich et al. |
| 2007/0299538 A1 | 12/2007 | Roeber |

(56) References Cited

U.S. PATENT DOCUMENTS

| | | |
|---|---|---|
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li et al. |
| 2009/0318752 A1 | 12/2009 | Evans et al. |
| 2010/0104608 A1 | 4/2010 | Abuzaina et al. |
| 2010/0137679 A1 | 6/2010 | Lashinski et al. |
| 2010/0318108 A1 | 12/2010 | Datta et al. |
| 2011/0015760 A1 | 1/2011 | Kullas |
| 2011/0054604 A1 | 3/2011 | Becker |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet et al. |
| 2011/0257666 A1 | 10/2011 | Ladet et al. |
| 2011/0257761 A1* | 10/2011 | Mortarino ............... D04B 1/22 623/23.72 |
| 2012/0004723 A1 | 1/2012 | Mortarino et al. |
| 2012/0016388 A1 | 1/2012 | Houard et al. |
| 2012/0029537 A1 | 2/2012 | Mortarino |
| 2012/0053690 A1 | 3/2012 | Frank |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell et al. |
| 2012/0179176 A1 | 7/2012 | Wilson et al. |
| 2012/0197415 A1 | 8/2012 | Montanari et al. |
| 2012/0226352 A1 | 9/2012 | Becker |
| 2012/0283826 A1 | 11/2012 | Moses et al. |
| 2013/0253645 A1 | 9/2013 | Kerr et al. |
| 2014/0044861 A1 | 2/2014 | Boey et al. |
| 2014/0100656 A1 | 4/2014 | Namnoum et al. |
| 2014/0222161 A1* | 8/2014 | Mathisen ............... A61F 2/0077 623/23.72 |
| 2014/0276993 A1 | 9/2014 | Reilly et al. |
| 2014/0364684 A1 | 12/2014 | Lecuivre et al. |
| 2015/0250574 A1 | 9/2015 | Egnelov |
| 2015/0351899 A1* | 12/2015 | Mortarino ............... A61F 2/0063 623/8 |
| 2016/0193026 A1* | 7/2016 | Mortarino ............... D04B 21/12 606/151 |
| 2016/0213456 A1* | 7/2016 | Mortarino ............... D04B 1/14 |
| 2016/0213457 A1* | 7/2016 | Mortarino ........... A61L 27/3604 |
| 2016/0242899 A1* | 8/2016 | Lee ............................. A61F 2/12 |
| 2017/0027678 A1* | 2/2017 | Greenhalgh .......... A61L 31/005 |
| 2017/0216009 A1* | 8/2017 | Felix ........................ A61F 2/12 |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 0544485 A1 | 6/1993 |
| EP | 0552576 A1 | 7/1993 |
| EP | 0611561 A1 | 8/1994 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 0827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 0898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1216717 A1 | 6/2002 |
| EP | 1216718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2612392 A1 | 9/1988 |
| FR | 2682284 A1 | 4/1993 |
| FR | 2715309 A1 | 7/1995 |
| FR | 2715405 A1 | 7/1995 |
| FR | 2724563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 B1 | 12/2005 |
| FR | 2876020 A1 | 4/2006 |
| FR | 2863277 B1 | 6/2006 |
| FR | 2884706 B1 | 4/2008 |
| FR | 2929834 A1 | 10/2009 |
| FR | 2953709 A1 | 6/2011 |
| GB | 1174814 A | 12/1969 |
| GB | 2051153 A | 1/1981 |
| GB | 2306110 A | 4/1997 |
| JP | H0332677 U | 3/1991 |
| JP | 05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| NZ | 563828 A | 9/2011 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9310731 A1 | 6/1993 |
| WO | 9311805 A1 | 6/1993 |
| WO | 9318174 A1 | 9/1993 |

(56) References Cited

FOREIGN PATENT DOCUMENTS

| | | | |
|---|---|---|---|
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 0181667 A1 | 11/2001 |
| WO | 0207648 A1 | 1/2002 |
| WO | 0217853 A2 | 3/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004096098 A1 | 11/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023414 A1 | 3/2006 |
| WO | 2007004214 A2 | 1/2007 |
| WO | 2008066883 A2 | 6/2008 |
| WO | 2009039373 A1 | 3/2009 |
| WO | 2009071998 A2 | 6/2009 |
| WO | 2009031035 A3 | 1/2010 |
| WO | 2010043978 A2 | 4/2010 |
| WO | 2007048099 A3 | 9/2010 |
| WO | 2011007062 A1 | 1/2011 |
| WO | 2011026987 A1 | 3/2011 |
| WO | 2011038740 A1 | 4/2011 |
| WO | 2014041577 A1 | 3/2014 |

OTHER PUBLICATIONS

Blondin, C. et al., "Inhibition of Complement Activation by Natural Sulfated Polysaccharides (Fucans) from Brown Seaweed," Molecular Immuol., Mar. 1994, pp. 247-253, 31(4).

Blondin, C. et al., "Relationships between chemical characteristics and anticomplementary activity of fucans," Biomatenals, Mar. 1996, pp. 597-603, 17(6).

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Chen, G. et al., "A Hybrid Network of Synthetic Polymer Mesh and Collagen Sponge," The Royal Society of Chemistry 2000, Chem. Commun., Jul. 2000, pp. 1505-1506.

Collins, R. et al., "Use of collagen film as a dural substitute: Preliminary animal studies," Journal of Biomedical Materials Research, Feb. 1991, pp. 267-276, vol. 25.

Communication pursuant to Article 94(3) EPC issued in European Patent Application No. 15305634.3 dated Nov. 13, 2019, 5 pages.

Dr. S. Raz, "The Karl Mayer Guide to Tehnical Textiles," Jan. 2000, pp. 1-36, Obertshausen, Germany.

European Search Report for EP 15305634.6 date of completion is Nov. 2, 2015 (3 pages).

Examination report No. 1 for standard patent application issued in Australian Application No. 2016201622 dated Mar. 3, 2020, 3 pages.

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, 7 pp. 189-201, 52(2), published online Nov. 2009.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Haroun-Bouhedja, F. et al., "Relationship between sulfate groups and biological activities of fucans," Thrombosis Res., Dec. 2000, pp. 453-459, 100(5).

Hirano, S. et al., "The blood biocompatibility of chitosan and N-acylchitosans," J. Biomed. Mater. Res., Apr. 1985, 413-417, 19.

Junge, K. et al., "Functional and Morphologic Properties of a Modified Mesh for Inguinal Hernia Repair," World J. Surg., Sep. 2002, pp. 1472-1480, 26.

Kanabar, V. et al., "Some structural determinants of the antiproliferative effect of heparin-like molecules on human airway smooth muscle," Br. J. Pharmacol., Oct. 2005, pp. 370-777, 146(3).

Klinge, U. et al., "Foreign Body Reaction to Meshes Used for the Repair of Abdominal Wall Hernias," Eur J. Surg, Sep. 1999, pp. 665-673, 165.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Langenbech, M. R. et al., "Comparison of biomaterials in the early postoperative period," Surg Endosc., May 2003, pp. 1105-1109, 17 (7).

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Malette, W. G. et al., "Chitosan, A New Hemostatic," Ann Th. Surg., Jul. 1983, pp. 55-58, 36.

Muzzarelli, R. et al., "Reconstruction of parodontal tissue with chitosan," Biomaterials, Nov. 1989, pp. 598-604, 10.

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Prokop, A. et al., "Water Soluble Polymers for Immunoisolation I: Complex Coacevation and Cytotoxicity," Advances in Polymer Science, Jul. 1998, pp. 1-51, 136.

Rao, B. et al., "Use of chitosan as a biomaterial: Studies on its safety and hemostatic potential," J. Biomed. Mater. Res., Jan. 1997, pp. 21-28, 34.

Rosen, M. et al., "Laparoscopic component separation in the single-stage treatment of infected abdominal wall prosthetic removal," Hernia, 2007, pp. 435-440, 11, published online Jul. 2007.

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220, 18(2).

Strand, S. et al., "Screening of Chitosans and Conditions for Bacterial Flocculation," Biomacromolecules, Mar. 2001, 126-133, 2.

Varum, K. et al., "In vitro degradation rates of partially N-acetylated chitosans in human serum," Carbohydrate Research, Mar. 1997, pp. 99-101, 299.

Welty, G. et al., "Functional impairment and complaints following incisional hernia repair with different polypropylene meshes," Hernia, Aug. 2001; pp. 142-147, 5.

Zvyagintseva, T. et al., "Inhibition of complement activation by water-soluble polysaccharides of some far-eastern brown seaweeds," Comparative Biochem and Physiol, Jul. 2000, pp. 209-215, 126(3).

(56) References Cited

OTHER PUBLICATIONS

Examination report No. 2 issued in Australian Patent Application No. 2016201622 dated Aug. 21, 2020, 4 pages.

* cited by examiner

PROSTHESIS FOR SUPPORTING A BREAST STRUCTURE

CROSS-REFERENCE TO RELATED APPLICATIONS

This application is a divisional of U.S. patent application Ser. No. 15/920,597 filed Mar. 14, 2018, which is a divisional of U.S. patent application Ser. No. 15/099,633 filed Apr. 15, 2016, now U.S. Pat. No. 9,931,198, which claims benefit of and priority to European Patent Application No. 153056354.6 filed Apr. 24, 2015, the disclosures of each of the above-identified applications are hereby incorporated by reference in their entirety.

BACKGROUND

1. Technical Field

The present invention relates to a prosthesis for supporting a breast structure, such as a breast implant or breast tissue within a patient.

2. Background of Related Art

Breast cancer is one of the most common cancers among women. If the disease is not caught early, it is common that large portions of breast tissue are removed. In a conventional procedure called mastectomy, one or both breasts are partially or completely removed in order to treat or subsequently prevent breast cancer. Since such procedures generally result in a substantial amount of tissue being removed, many women will then opt for breast reconstructive surgery in order to reform the breast into a natural looking state. It is often acknowledged that the process of cancer treatment and removal of breast tissue can weigh heavily not only on the patients physical but also emotional well being. Thus, such surgery to reconstruct the breast can allow the patient to maintain self confidence after such an ordeal.

With reference to FIG. 1 is shown a healthy breast 1. The breast 1 is formed of fat tissue 3 encompassing lobules 4 and milk ducts 5 converging towards the nipple-areola complex 2. With reference to FIG. 1, are further shown the inframammary fold 6 which defines the lower end of the breast 1, the pectoral muscle 7, the chest wall 8 formed of the ribs 9 and of the intercostal muscles 10, and eventually the skin 11.

Within the framework of a mastectomy, lobules 4 and milk ducts 5 are removed from the breast 1.

SUMMARY

Many techniques of breast reconstruction are known in the art. Such procedures generally involve employment of implants, one's own body tissue, or a combination thereof, which are employed for reforming the breast. Implants are the most common technique known in the art and are used for reconstructive surgery. This involves the employment of silicon, saline, or other suitable material formed implants which may be placed under the pectoral muscle (submuscular) for forming and shaping the breast.

With reference to FIG. 2, is shown a reconstructed breast 1, in which the lobules and milk ducts have been removed and replaced by a breast implant 12 which is placed under the pectoral muscle 7. As shown on this figure, the breast implant 12 has the global shape of a water drop with a curve-shaped lower portion and a substantially conical upper portion.

Because of the weakening of the biological tissues around the breast implant due to mastectomy, it may happen that after some time, the breast implant bottoms out, in other words moves downwards under the effect of natural gravity. Such a phenomenon often requires surgery in order to either remove the implant or reposition it correctly. For these reasons, implant-based breast reconstruction is usually used in combination with an implantable material intended to provide a layer of long-term support for the breast implant, for enhanced and shape of the breast, such implantable material generally having the shape of a sling and acting as an internal bra.

Moreover, independently from medical reasons such as breast cancer, many women may decide to undergo breast surgery on a healthy breast in order to lift up the breast for purely aesthetic reasons. In such a case, no part of the biological breast tissue is removed, and a material such as a tape or a sling is implanted underneath the breast in order to lift it up and to support it.

The use of medical surgical mesh material as a support member for a breast structure is known in the art. In the present application, by «breast structure» is meant both a breast implant, replacing the removed biological breast tissue in case of reconstruction of a breast after a breast cancer, or the natural biological breast tissue, in case of purely aesthetic surgery. Conventionally, the surgical mesh is provided as a flat substantially rectangular or square sheet that the physician must accurately cut to size in an attempt to fit the natural curvature of a breast and to provide adequate support for the breast structure.

These square or rectangular sheets of mesh fabric are neither configured to size nor cut to shape to form the proper three dimensional shape when placed in a supportive engagement in an arc under the breast implant. Surgeons must take valuable time and cut the fabric sheet in the operating room during the procedure. In particular, the surgeon must cut the mesh and use trial by error in order to achieve the best form-fitting shape. This is time-consuming and fastidious for the surgeon, and unconfortable for the patient. This need for cutting mesh fabric may result in uneven or miss-cut sheets of mesh which are then implanted and must be forcefully stretched or manipulated into a "fitted" engagement to the breast of the patient. To maintain this fitted engagement, the surgeon resorts to sutures through the mesh and into surrounding tissue. It may also happen that the surgeon has to fold parts of the mesh on itself, thereby creating additional thickness resulting in an improper fit around the curved area of the breast tissue or implant and possible painful feeling for the patient. Folds may also cause unnatural appearance.

In addition, the dimensions and configurations of the mesh for each breast will vary widely for each instance of the procedure and the desired outcome of breast size, shape, and form. The lack of customized supporting prosthesis for breast implants can adversely effect the finished shape and feel of the reconstructed breast tissue. Patients may suffer from discomfort from the material compressing the breast tissue or implant, or from a distaste for the visual aspects of the finished surgery. Patients may require further surgeries to correct any inconsistencies with the mesh, or may just unfortunately live with the uncomfortable current state of the reconstruction.

Moreover, the conventional synthetic mesh materials used today make no provision for accommodating stretch in one or both directions on a controlled basis. Known devices may therefore fail in providing adequate support and comfort in the natural movement and feel of the breast which for each human is of a custom dimension and area. This poor fit and lack of elasticity may result in additional surgeries to correct such inconsistencies.

The stiffness of surgical mesh conventionally employed with breast reconstructive surgery can seriously inhibit the natural look, movement, and feel of the breast tissue and such is undesirable. Further, stiff materials formed into meshes can prove more difficult to handle by the physician during implantation due to the need to customize the planar sheet, to fit the curved three dimensional shape of a breast. Such misfitting sheets customized in the operating room may require additional suturing to maintain their position in the body.

There is therefore a need for a prosthesis capable of supporting a breast structure, such as a breast implant post mastectomy or the biological breast tissue in an aesthetic surgery, said breast structure being a non planar body having three-dimensional curves, in a manner that would be the closest as possible to the natural biological support, regarding on one hand strength of the support in order to avoid sagging of the supported breast structure, and on the other hand elasticity of such support in order to provide a comfortable feeling to the patient. In case the breast structure is a breast implant, there is also a need for such a supporting prosthesis that would securely hold the breast implant in order to limit the risk of bottoming out of the implant. There is also a need for a prosthesis for supporting a breast structure that would allow the surgeon to try several positions of the prosthesis relative to the breast structure and to the pectoral muscle before secure fixation. The prosthesis should therefore be preferably repositionable.

In this application, the "upper" end, edge or part of an element of a prosthesis is to be understood as meaning the end, edge or part of the element located substantially in the direction of the head of the body when the prosthesis is implanted in the body. The "lower" end, edge or part of an element of a prosthesis is to be understood as meaning the end, edge or part of the element located in the direction of the feet of the body when the prosthesis is implanted in the body. Likewise, in this application, the "vertical direction" is to be understood as meaning the direction aligned on the feet-head axis of a body, and the «horizontal direction» is to be understood as being the transversal direction of the vertical direction in a plane of the prosthesis.

A first aspect of the invention is a prosthesis for supporting a breast structure within a patient, the prosthesis comprising:

a reinforcement part comprising a first fabric made of a first arrangement of biocompatible yarns and configured to receive at least a curve-shaped lower portion of the breast structure, said reinforcement part being intended to be sutured to the chest wall or to the infra-mammary fold, said first arrangement of yarns conferring to said first fabric an elongation under 50N in the vertical direction of E1, a fixation part comprising a second fabric made of a second arrangement of biocompatible yarns and intended to be fixed to the pectoral muscle, said second arrangement of yarns conferring to said second fabric an elongation under 50N in the vertical direction of E2, and a transition part comprising a third fabric made of a third arrangement of biocompatible yarns, said transition part connecting together the reinforcement part and the fixation part, said third arrangement of yarns conferring to said third fabric an elongation under 50N in the vertical direction of E3, wherein E3 is greater than E1 and greater than E2.

In the present application, by arrangement of biocompatible yarns is meant an assembly of yarns, fibres, filaments and/or multifilaments forming a fabric, and for example obtained by knitting, weaving, braiding, or non-woven.

In the present application, "biocompatible" is understood as meaning that the materials having this property can be implanted in the human or animal body.

The prosthesis of the invention may be provided to the user as a textile in a preformed perimeter shape, said textile encompassing the first, second and third fabrics. The prosthesis of the invention is intended to be used as a support of a breast structure in breast reconstructive surgery or in breast lifting surgery and is intended to engage around the breast structure, such as the breast implant or the breast tissue, so as to cup said breast structure, and at least part of its peripheral edge is intended to be sutured either to the chest wall, for example the ribs, and/or to the pectoral muscle. The prosthesis of the invention provides a shape and configuration providing the most support when curved in a supportive engagement with the breast structure.

Because of its structure comprising at least three parts and because of the relative values of the respective elongations under 50N in the vertical direction of these three parts, the prosthesis of the invention allows for stretching and elasticity of the supported breast structure, in a manner very close to the natural behavior of a breast, thereby yielding a more natural appearance and movement during movement such as walking by the patient. The prosthesis of the invention provides excellent support to the multi directional curves of the supported breast structure.

The prosthesis of the invention comprises three parts, one of which, the transition part, shows an elongation under 50N in the vertical direction E3 greater than the elongation under 50N in the vertical direction E1 and E2 of each of the two other parts, namely the reinforcement part and the fixation part. For example, the value of E3 is above the value of E1 and above the value of E2, and E3 may not be equal to E1 and may not be equal to E2.

The elongation under 50N in the vertical direction of each of the three parts of the prosthesis is provided to said part by the arrangement of yarns defining the fabric forming said part. In particular, for each fabric, the elongation under 50N in the vertical direction is dependent both on the nature of the yarns and on the pattern followed by the yarns. For example, the pattern may be a woven pattern or a knitting pattern. It is known that knits and woven structures possess a warp direction and a weft direction. For knits and wovens, elongations under 50N are measured both in the warp and in the weft directions. Depending on the weaving or knitting patterns applied and on the nature of the yarns used, the elongation under 50N in the warp direction may be different from the elongation under 50N in the weft direction for a single fabric.

In the present application, by "elongation under 50N in the vertical direction" for a fabric of the prosthesis of the invention, is meant either the elongation under 50N measured in the warp direction of the fabric or the elongation under 50N measured in the weft direction of the fabric, depending on which direction of the fabric, either warp or weft, is positioned along the vertical direction of the prosthesis.

In the present application, the elongation under 50N in the warp direction and in the weft direction of a fabric is measured according to the method for measuring the tensile breaking strength and elongation at break according to ISO 13934-1: 2013 *"Textiles—Tensile properties of fabrics—Part 1: Determination of maximum force and elongation at maximum force using the strip method"*, 5 samples, width: 50 mm, Length: 200 mm between the jaws, Crosshead speed: 100 mm/min, Pre-load: 0.5 N, using a traction testing machine such as the Hounsfield model H5KS (Hounsfield, Redhill, England).

The reinforcement part of the prosthesis of the invention is intended to receive the curve-shaped lower portion of a breast implant and is intended to be sutured to the chest wall, for example to the ribs, or to the infra-mammary fold. The reinforcement part of the prosthesis of the invention is therefore intended to behave as a hammock and should have mechanical properties sufficient for contributing to the support of the breast implant against gravity and for example for limiting the risk of bottoming out of the breast implant. In this view, the first fabric forming the reinforcement part should show an elongation under 50N in the vertical direction, also referred to as E1, adapted to hold the breast implant in a relatively steady and reliable manner.

For example, E1 may be equal or less than about 40%. For example E1 may range from about 0 to about 40%, preferably from about 18% to about 35%.

The fixation part of the prosthesis of the invention is intended to be fixed to the pectoral muscle. The fixation part is intended to face the top portion of the breast structure and should show mechanical properties adapted to secure anchorage of the prosthesis in the pectoral muscle. In this view, the second fabric forming the fixation part should show a limited elongation under 50N in the vertical direction, also referred to as E2, so that anchorage in the pectoral muscle and tissue ingrowth are not negatively impaired by an excessive solicitation.

For example, E2 may be equal or less than about 35%. For example E2 may range from about 0% to about 35%, preferably from about 5% to about 15%.

The transition part of the prosthesis of the invention is intended to connect the reinforcement part to the fixation part so as to absorb the tensions created by the mechanical pressures of the supported breast structure and limit the pain felt by the patient, and so as to further allow the supported breast structure to have the most natural mechanical behavior. The transition part may preferably represent a limited area of the whole prosthesis and the third fabric forming the transition part should show an elongation under 50N in the vertical direction, also referred to as E3, adapted to give the supported breast structure some freedom of movement and to absorb gently the tensions generated in the supported breast structure by the movements of daily life. In particular, E3 is greater than E1 and than E2 so as to have the capability to absorb the tensions originating from the first fabric and the second fabric due to the respective functions of support and of fixation of the reinforcement part and of the fixation part.

For example, E3 is equal or greater than about 35%. In embodiments, E3 ranges from about 35% to about 120%, preferably from about 35% to about 70%.

The transition part of the prosthesis of the invention allows the prosthesis to accommodate the curve of the breast structure in a natural and comfortable fashion for the patient. The elongation under 50N in the vertical direction of the third fabric forming the transition part confers to the supported breast structure the required elasticity and stretch to allow the breast structure to move in a natural manner which is comfortable to the patient.

The prosthesis of the invention may be under the form of various embodiments, for example defined by the following features, taken in combination or as alternatives:

E1 may be equal or less than about 40%, for example E1 may range from about 0 to about 40%, preferably from about 18% to about 35%, E2 may be equal or less than about 35%, for example E2 may range from about 0% to about 35%, preferably from about 5% to about 15%, E3 may be equal or greater than about 35%, for example E3 may range from about 35% to about 120%, preferably from about 35% to about 70%, E3 may be more than 20%, 30%, 50%, 100%, 200% greater than E1, E3 may be more than 50%, 100%, 200%, 500% greater than E2, where H represents the total height of the prosthesis and h the height of the transition part, measured along the vertical direction, when said prosthesis is in a planar configuration, the ratio h/H ranges from about 1/30 to about 1/2, preferably from about 1/12 to about 1/4, the reinforcement part may have a globally elongated shape in the horizontal direction, said shape showing a convex lower edge, the shape of the reinforcement part may show a convex upper edge, the shape of the reinforcement part may show a concave upper edge, the transition part may have substantially the shape of a portion of a circular crown, the lower edge of the shape of the transition part may be the upper edge of the shape of the reinforcement part, the fixation part may comprise a lower edge from which extend vertically and in the upper direction one or more arm(s) intended to be fixed to the pectoral muscle, each arm of the fixation part having a lower end and an upper end, said lower end may be substantially larger in the horizontal direction than said upper end, at least two said arms of the fixation part may extend vertically and in the upper direction, at least three said arms of the fixation part may extend vertically and in the upper direction, at least four said arms of the fixation part may extend vertically and in the upper direction, at least five said arms of the fixation part may extend vertically and in the upper direction, at least six said arms of the fixation part may extend vertically and in the upper direction, at least seven said arms of the fixation part may extend vertically and in the upper direction, at least eight said arms of the fixation part may extend vertically and in the upper direction, the lower edge of the fixation part may be the upper edge of the shape of the transition part, a recess may be provided in one or more said reinforcement part, fixation part and transition part, said recess being intended to face the nipple-areola complex when the prosthesis is implanted, the first fabric may be a porous knit, the first fabric may be a two-dimensional porous knit, the first fabric may be a three-dimensional porous knit, the first fabric may be a porous knit showing pores having a size above 1 mm×1 mm, the first fabric may show a bursting strength above about 400 kPa, the yarns forming the first arrangement may be monofilaments, the yarns forming the first arrangement may be monofilaments having a diameter of less than about 0.3 mm, the yarns forming the first arrangement may be multifilaments, for example having a linear density of less than about 400 dTex, the yarns forming the first arrangement may be surface treated with an low friction substance, a face of the first fabric intended to be in contact with the breast implant may be covered with a low friction coating, for example a low friction film, the first fabric being a three-dimensional porous knit, a face of said three-dimensional knit intended to be in contact with the breast structure may be covered with a low friction coating, for example a low friction film, and a face of said three-dimensional knit intended to be in contact with the skin may be provided with pores having a size above 1 mm×1 mm, the height h of the transition part may range from 1 to 5 cm, preferably from 2 to 3 cm, the third fabric may be a porous knit, the third fabric may be a two-dimensional porous knit, the yarns forming the third arrangement may be monofilaments, the yarns forming the third arrangement may be multifilaments, the second fabric may be a porous knit, the second fabric may be a two-dimensional porous knit, a face of the second fabric intended to face the pectoral muscle may be provided with fastening means capable of fixing at least temporarily said face of said second fabric in the pectoral muscle, the reinforcement part may be provided with a reinforcement member configured for inducing a curved shape to said first fabric conformable with said curve-shaped lower portion of the breast structure, the reinforcement member may be an overmolded wire positioned in the area of a lower edge of said reinforcement part, the reinforcement member may be made from a bioresorbable material, the reinforcement part may be linked to the transition part by means of sewing, gluing welding, overmolding and combinations thereof, the transition part may be linked to the fixation part by means of sewing, gluing, welding, overmolding and combinations thereof, the first, second and third fabrics may be made as a single unitary structure, h being the height of the transition part, h1 being the height of the reinforcement part, h2 being the height of the fixation part, all measured along the vertical direction when said prosthesis is in a planar configuration, the ratio h/h1 may range from about 1/15 to about 2/1, preferably from about 1/6 to about 1/1, and the ratio h/h2 may range from about 1/15 to about 2/1, preferably from about 1/6 to about 1/1.

In embodiments, wherein H represents the total height of the prosthesis and h the height of the transition part, measured along the vertical direction, when said prosthesis is in a planar configuration, the ratio h/H ranges from about 1/30 to about 1/2, preferably from about 1/12 to about 1/4. Such a ratio allows obtaining the adequate stretch and elasticity for conferring to the prosthesis a behavior close to the natural behavior of a natural breast while not jeopardizing the strength of the support needed to hold the breast structure in place against gravity. In particular, when the breast structure to be supported is a breast implant, such a ratio contributes to avoid bottoming out of the implant and sagging of the reconstructed breast.

The required elongation under 50N in the vertical direction may be provided to each fabric of the prosthesis of the invention by means of use of specific yarns such as elastic yarns, which may be combined or not with conventional non elastic yarns, and/or by means of specific arrangement of yarns, such as the weaving and knitting patterns.

Examples of elastic yarns particularly suitable for the third fabric of the prosthesis of the invention may be selected from the group consisting in polyether amide yarns, polyurethane yarns or thermoplastic elastomer polyethylene terephthalate yarns, having an elongation at break equal to or greater than 75%, measured according to ISO 2321:2006.

For example, non elastic yarns may show an elongation at break of less than 30% measured according to ISO 2062: 2010.

The yarns or fibres or filaments, monofilaments and/or multifilaments forming the arrangement of yarns constituting the first, second and third fabrics of the prosthesis according to the invention can be made of any biodegradable or non-biodegradable biocompatible material.

In the present application, "bioresorbable" or "biodegradable" is understood to mean that the materials having this property are absorbed and/or degraded by the tissues or washed from the implantation site and disappear in vivo after a certain time, which may vary, for example, from a few hours to a few years, depending on the chemical nature of the materials.

Thus, the biodegradable materials suitable for the yarns of the first, second and third fabrics of the prosthesis according to the present invention can be chosen from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these compounds and mixtures thereof.

The non-biodegradable materials suitable for the yarns of the first, second and third fabrics of the prosthesis according to the present invention can be chosen from polyethylene terephthalate (PET), polyamides, aramids, expanded polytetrafluoroethylene, polyurethane, polyvinylidene difluoride (PVDF), polybutyl esters, polyetheretherketone (PEEK), polyolefins (such as polyethylene or polypropylene), polyethers, and combinations thereof.

For each fabric, the arrangement of yarns may be a knit, a woven structure, a braid or a non-woven. In embodiments, the fabric of the reinforcement part, the fabric of the fixation part and the fabric of the transition part of the prosthesis of the invention are knits, in particular porous knits.

In the present application, the term "porous knit" is intended to mean a knit which has pores, or gaps, alveoli, holes, orifices, which are evenly or unevenly distributed not only at the surface, but also within the thickness of said knit. Indeed, by virtue of the meshwork of a knit in general, it is possible to obtain openworked faces that promote cell recolonization after implantation, namely a porous knit.

For example, the first knit may be a porous knit. The second fabric may be a porous knit. The third fabric may be a porous knit. In embodiments, each of said first, second and third fabrics are porous knits. The porous knits suitable for the first, second and third fabrics of the prosthesis of the invention may show various knitting patterns conferring to each knit specific mechanical properties.

The porous knits suitable for the prosthesis of the invention may be two-dimensional or three-dimensional.

Within the meaning of the present application, a two-dimensional knit is understood as a knit having two opposite faces linked to each other by meshes but devoid of a spacer giving it a certain thickness: such a knit can be obtained, for example, by knitting yarns on a warp knitting machine or raschel knitting machine using two guide bars. Examples of knitting two-dimensional knits suitable for the present invention are given in the document WO2009/071998.

According to the present application, a three-dimensional knit is understood as a knit having two opposite faces linked to each other by a spacer that gives the knit a significant thickness, said spacer itself being formed from additional linking yarns in addition to the yarns forming the two faces of the knit. Such a knit can be obtained, for example, on a double-bed warp knitting or raschel knitting machine using several guide bars. Examples of knitting three-dimensional knits suitable for the present invention are given in the documents WO99/05990, WO2009/031035 and WO2009/071998.

The first fabric may be a two-dimensional porous knit. A two-dimensional knit may confer a good mechanical strength to the first fabric and therefore to the reinforcement part.

Alternatively, the first fabric may be a three-dimensional porous knit. A three-dimensional porous knit allows a high degree of differentiation of its two opposite faces and therefore allows providing a knit having a first property on a first face, such as for example a smooth surface for contact with the breast structure such as a breast implant, and having a different property on its opposite face, such as a porosity adapted for promoting cell growth with regards to the facing skin tissues.

In embodiments, the first fabric is a porous knit showing pores having a size above 1 mm×1 mm. For example, the pore size of the porous knit forming the third fabric may range from 1 mm×1 mm to 3 mm×3 mm.

In the present application, the pore size (width×height) (mm) is measured according to the following method: knit biggest pores are measured making one measurement on 10 individual samples with a profile projector such as a projector 300V from ORAMA.

The first fabric forming the reinforcement part is intended to be positioned between the breast structure and the skin once the prosthesis is implanted. The presence of large pores on the face of the knit forming the first fabric intended to face the skin will favor cell colonization once the prosthesis is implanted.

In embodiments, the first fabric shows a thickness ranging from 0.2 mm to 2.5 mm. Such a thickness allows the reinforcement part to be less palpable under the skin, thereby conferring to the patient a natural feeling regarding the supported breast structure.

In embodiments, the first fabric shows a bursting strength above about 400 kPa.

In the present application, the bursting strength (kPa) is measured according to ISO 13938-2: 1999 "Textiles—Bursting properties of textiles—Pneumatic method for determining the bursting strength and bursting deformation", 5 samples.

Such a bursting strength allows the reinforcement part to complete adequately its function of support. In particular, such a bursting strength allows the reinforcement part to hold securely the breast structure, even when the patient performs significant movement of the daily life, such as jumping, and to compensate the undesired effect of gravity on the breast structure.

In embodiments, the first fabric shows a suture pull out strength in the warp direction and in the weft direction above about 15N, preferably above about 35N.

In the present application, the suture pull out strength in the warp direction and in the weft direction is measured according to NF S94-801: 2007 "Reinforcement implants introduced by the vaginal route for the treatment of stress urinary incontinence and/or of prolapse of the pelvic organs—pre-clinical trials and clinical trials"—§ 5.3.3 5 specimens 50×100 mm, USP 2 suture yarn, crosshead speed: 100 mm/min, using a traction testing machine such as the Hounsfield model H5KS (Hounsfield, Redhill, England).

Such a suture pull out strength in the warp direction and in the weft direction allows in particular the reinforcement part to be sutured in a reliable manner to the chest wall, for example the ribs, or to the infra-mammary fold.

In embodiments, the first fabric shows a tear strength in the warp direction and in the weft direction above about 25N, preferably above about 32N.

In the present application, the tear strength (N) in the warp direction and in the weft direction is measured according to ISO 4674:1977 *"Textiles covered with rubber or plastic—Determination of the tear strength"* Method A2, 5 samples, width: 75 mm, Tear length ≤145 mm, crosshead speed: 100 mm/min.

Such a tear strength in the warp direction and in the weft direction allows in particular the reinforcement part to resist efficiently to tensions generated in the breast structure, in particular in the reconstructed breast by the weight of the breast implant.

The yarns forming the first arrangement may be any biocompatible yarns known for forming surgical meshes, such as fibers, monofilaments, multifilaments and combinations thereof.

In embodiments, the yarns forming the first arrangement are multifilaments. Multifilaments may provide a soft touch to the knit and allow obtaining a more natural palpation feeling as well as a more natural appearance of the supported breast structure.

In embodiments, the yarns forming the first arrangement are monofilaments. For example, the monofilaments forming the first arrangement show a diameter of less than about 0.3 mm. Such monofilaments with a small diameter are less palpable under the skin and therefore confer a more natural feeling on the skin of the patient.

A first example of a porous knit suitable for forming a first fabric for the reinforcement part of the prosthesis of the invention is a knit obtained by knitting a monofilament yarn of polyethylene terephthalate of diameter 0.08 mm on a double bed knitting machine with four guide bars, GBII, GBIII, GBIV and GBV, according to the following pattern, according to ISO 11676 standard:

GBII: 4.3.2.2/1.0.1.1/1.2.1.1/1.0.1.1/1.2.1.1/1.0.1.1/1.2.3.3/4.5.4.4/4.3.4.4/4.5.4.4/4.3.4.4/4.5.4.4//

GBIII: 3.4.8.9/6.7.6.6/6.5.6.6/6.7.6.6/6.5.6.6/6.7.6.6/6.5.1.0/3.2.3.3/3.4.3.3/3.2.3.3/3.4.3.3/3.2.3.3//

GBIV: 4.4.4.3/2.2.1.0/1.1.1.2/1.1.1.0/1.1.1.2/1.1.1.0/1.1.1.2/3.3.4.5/4.4.4.3/4.4.4.5/4.4.4.3/4.4.4.5//

GBV: 1.1.1.2/3.3.4.5/4.4.4.3/4.4.4.5/4.4.4.3/4.4.4.5/4.4.4.3/2.2.1.0/1.1.1.2/1.1.1.0/1.1.1.2/1.1.1.0//

This knit is a three-dimensional knit and will be referred to hereinafter as Knit X.

Knit X shows the following properties, measured according to the methods as described in the present application:

E1: 25%, corresponding to the elongation under 50N of the knit in the warp direction of the knit.

Elongation under 50N of the knit in the weft direction: 40%

Bursting strength: 415 kPa

Suture pull out strength in the warp direction and in the weft direction: 37 N

Tear strength in the warp direction and in the weft direction: 35N

Pore size: 2.1 mm×3.0 mm

Another example of a porous knit suitable for forming a first fabric for the reinforcement part of the prosthesis of the invention is a knit obtained by knitting a multifilament yarn of polyethylene terephthalate of 50 dTex on a double bed knitting machine with six guide bars, GBI, GBII, GBIII, GBIV, GBV and GBVI, according to the following pattern, according to ISO 11676 standard:

GBI: 1.2.1.1/1.0.1.1/1.2.1.1/1.0.1.1/1.2.2.2/3.2.2.2/1.2.2.2/3.2.2.2//

GBII: 1.2.2.2/3.2.2.2/1.2.2.2/3.2.2.2/1.2.1.1/1.0.1.1/1.2.1.1/1.0.1.1//

GBIII: 0.1.0.1/0.0.0.0//

GBIV: 0.1.0.1/0.0.0.0//

GBV: 1.1.0.1/1.1.2.1/1.1.0.1/11.1.2.1/2.2.2.3/2.2.2.1/2.2.2.3/2.2.2.1//

GBVI: 2.2.2.3/2.2.2.1/2.2.2.3/2.2.2.1/1.1.0.1/1.1.2.1/1.1.0.1/1.1.2.1//

This knit is a three-dimensional knit and will be referred to hereafter as Knit Y.

Knit Y shows the following properties measured according to the methods as described in the present application:

E1: 19%, corresponding to the elongation under 50N of the knit in the warp direction of the knit.

Elongation under 50N of the knit in the weft direction: 44%

Bursting strength: 321 kPa

Suture pull out strength in the warp direction, respectively in the weft direction: 24N, respectively 33 N.

Tear strength in the warp direction and in the weft direction: 20 N

Pore size: 1.9 mm×2.4 mm

Another example of a porous knit suitable for forming a first fabric for the reinforcement part of the prosthesis of the invention is a knit obtained by knitting a monofilament yarn of polypropylene of a diameter of 0.10 mm on a double bed knitting machine with four guide bars, GBII, GBIII, GBIV and GBV, according to the following pattern, according to ISO 11676 standard:

GBII: 0.1.1.1/1.2.2.2/3.4.4.4/5.4.4.4/4.3.3.3/2.1.1.1//

GBIII: 5.4.4.4/4.3.3.3/2.1.1.1/0.1.2.1/1.2.2.2/3.4.4.4//

GBIV: 4.4.5.4/4.4.4.3/3.3.2.1/11.1.0.1/1.1.1.2/2.2.3.4//

GBV: 1.1.0.1/1.1.1.2/2.2.3.4/4.4.5.4/4.4.4.3/3.3.2.1//

This knit is a three-dimensional knit and will be referred to hereafter as Knit Z.

Knit Z shows the following properties measured according to the methods as described in the present application:

E1: 35%, corresponding to the elongation under 50N of the knit in the warp direction of the knit.

Elongation under 50N of the knit in the weft direction: 45%

Bursting strength: 646 kPa

Suture pull out strength in the warp direction and in the weft direction: 60 N

Tear strength in the warp direction and in the weft direction: 43 N

Pore size: 1.5 mm×1.5 mm

In embodiments, the yarns forming the first arrangement are surface treated with a low friction substance.

Within the meaning of the present application, "low friction" is understood as a smooth biocompatible material or coating.

Such embodiments allow obtaining a first fabric showing a low friction surface. The contact between the first fabric of the reinforcement part and the breast structure, for example the surface of the breast implant, will therefore be facilitated and will not favor friction, thereby limiting potential erosion with time.

Low friction substance for treating the yarns of the first arrangement may be selected from silicone, collagen and combinations thereof. Biocompatible spinning oil used in the textile field may also be used as a low friction substance for treating the yarns of the first arrangement.

Alternatively or in combination, a face of the first fabric intended to be in contact with the breast structure may be covered with a low friction coating, for example a low friction film. Such embodiments will favor easy contact between the surface of the breast structure, for example the breast implant and the first fabric and will limit erosion between these two elements. Potential degradation of the breast structure at the contact of the reinforcement part over time will therefore be avoided or limited.

A low friction film suitable for coating the face of the first fabric intended to be in contact with the breast structure may for example be a collagen film. Films obtained by extrusion from a copolymer of glycolide, caprolactone, trimethylene carbonate and lactide may also be used as a low friction film for coating the face of the first fabric intended to be in contact with the breast structure.

In embodiments, the first fabric is a three-dimensional porous knit, and a face of said three-dimensional knit intended to be in contact with the breast structure is covered with a low friction coating, for example a low friction film, and a face of said three-dimensional knit intended to be in contact with the skin is provided with pores having a size above 1 mm×1 mm. Such embodiments allow having different properties on each face of the knit, each property being in harmony with the function said face of the knit is intended to perform. The thickness of the three dimensional knit allows differentiating significantly the two opposite faces of the knit. As such, the face of the knit intended to be in contact with the breast structure is provided with a smooth surface thanks to the presence of the low friction coating and will enable a smooth contact with the breast structure, for example the breast implant, limiting the risk of erosion and degradation of the breast structure over time. Moreover, simultaneously, the large pores of the face of the knit intended to face the skin will favor cell colonization and cell growth within the three-dimensional knit.

The second fabric, which forms the fixation part, may be a two-dimensional porous knit. A two-dimensional knit may confer a good mechanical strength to the second fabric and therefore to the fixation part.

In particular, for the second fabric, it is possible to use patterns, such as chain stitched patterns, that are known for producing "blocked" knit, in other words knits usually showing a very low elongation at break, when only non elastic yarns are used. Such patterns producing "blocked knits" are useful when mechanical properties such as a good suture pull out and a good tear strength are needed. Such patterns produce fabrics having good mechanical resistance and limited elongation under 50N in the weft and warp directions.

In embodiments, the second fabric is a porous knit showing pores having size above 1 mm×1 mm. For example, the pore size of the porous knit forming the second fabric may range from 1 mm×1 mm to 3 mm×3 mm.

The second fabric forming the fixation part is intended to be positioned between the breast implant and the pectoral muscle once the prosthesis is implanted. The presence of large pores on the face of the knit forming the second fabric intended to face the pectoral muscle will favor cell colonization once the prosthesis is implanted.

In embodiments, the second fabric shows a thickness ranging from 0.2 mm to 2.5 mm. Such a thickness allows the fixation part to be less palpable under the skin, thereby conferring to the patient a natural feeling regarding the supported breast structure.

In embodiments, the second fabric shows a suture pull out strength in the warp direction and in the weft direction above about 20 N, preferably above about 30 N.

Such a suture pull out strength in the warp direction and in the weft direction allows in particular the fixation part to be sutured in a reliable manner to the pectoral muscle.

In embodiments, the second fabric shows a tear strength in the warp direction and in the weft direction above about 15 N, preferably above about 18 N.

Such a tear strength in the warp direction and in the weft direction allows in particular the fixation part to resist efficiently to tensions generated into said fixation part by the effect of gravity on the breast structure.

In embodiments, a face of said second fabric intended to face the pectoral muscle is provided with fastening means capable of fixing at least temporarily said face of said second fabric in the pectoral muscle. For example, these fastening means are barbs protruding from the face of the second fabric intended to be positioned in regards of the pectoral muscle. These fastening means or barbs can protrude from said face of said second fabric in a manner substantially perpendicular to the plane of said face or, alternatively, in one or more planes inclined with respect to the plane of said face. These barbs are intended to function as fixing means by anchoring themselves in the pectoral muscle.

By virtue of the fastening means, such as barbs, the second fabric of the prosthesis of the invention fixes naturally at least temporarily to the pectoral muscle. In particular, the surgeon may grip and ungrip the second fabric to the pectoral muscle as many times as necessary until he determines, optionally with the help of the patient, the right position for the fixation.

The fastening means, for example the barbs, of the second fabric of the prosthesis according to the invention can be formed from yarns, for example hot-melt monofilament yarns issuing directly from the arrangement of yarns forming the fabric. Fabrics and barbs of this kind, and the method of producing them, are described, for example, in the applications WO01/81667 and DE 198 32 634 or in the U.S. Pat. Nos. 6,596,002 and 5,254,133.

For example, the barbs are formed from monofilament yarns made of polylactic acid.

Alternatively, the fastening means, for example the barbs, of the second fabric of the prosthesis according to the invention can be any kind of hook made entirely from biocompatible material and integral with the arrangement of yarns forming said fabric, irrespective of whether these hooks have been incorporated in said fabric during the manufacture (braiding, knitting, weaving, etc.) of said arrangement of yarns or have been attached later.

Knits with barbs suitable for the second fabric of the prosthesis of the present invention are described in WO01/81667, for example, or are also commercially available from the company Sofradim Production under the trade name Parietex® Progrip or Parietene® Progrip.

In one embodiment, the second fabric is a knit based on at least a first yarn of biocompatible polymer material defining a first and second faces of the second fabric and at least a second biocompatible hot-melt monofilament yarn forming said fastening means by melting of loops generated by said second yarn, the pattern followed for knitting said first and second yarns on a warp knitting machine with three guide bars B1, B2, B3 being the following, according to the standard ISO 11676:

Bar B1: 1.0/0.1//
Bar B2: 1.0/7.7/6.6/7.7//
Bar B3: 2.1/5.5/3.4/0.0//
said second yarn following the pattern chart of bar B3.

This knit is a two-dimensional knit and will be referred to as Knit F. Knit F shows the following properties:

E2: 5%, corresponding to the elongation under 50N of the knit in the warp direction.

Elongation under 50N of the knit in the weft direction: 15%

Suture pull out strength in the warp direction and in the weft direction: 44 N in the warp direction, and 30 N in the weft direction Tear strength in the warp direction and in the weft direction: 28 N in the warp direction and 18 N in the weft direction Pore size: 1.8 mm×1.8 mm The third fabric, which forms the transition part, may be a two-dimensional porous knit. A two-dimensional knit may confer a good mechanical strength to the second fabric and therefore to the transition part.

In embodiments, the third fabric shows an elongation under 50 N in the warp direction equal or greater than about 35%. In embodiments, the third fabric shows an elongation under 50 N in the warp direction ranging from about 35% to about 120%.

In embodiments, the third fabric shows an elongation under 50 N in the weft direction equal or greater than about 35%. In embodiments, the third fabric shows an elongation under 50 N in the weft direction ranging from about 35% to about 120%.

Such elongation under 50 N in the weft direction and in the warp direction allow the third fabric to show an elongation under 50 N in the vertical direction of at least 35% and to confer to the transition part the required elasticity and stretch to perform its function of absorbing the tensions generated by the supported breast structure.

In embodiments, the third fabric is a porous knit showing pores having a size above 1 mm×1 mm. For example, the pore size of the porous knit forming the third fabric may range from 1 mm×1 mm to 3 mm×3 mm.

The third fabric forming the transition part is intended to be positioned between the breast structure and a lower region of the pectoral muscle once the prosthesis is implanted. The presence of large pores on the face of the knit forming the third fabric intended to face the lower region of the pectoral muscle will favor cell colonization once the prosthesis is implanted.

In embodiments, the third fabric shows a tensile breaking strength in the warp direction and in the weft direction equal or greater than 115 N. In embodiments, the third fabric shows a tensile breaking strength in the warp direction and in the weft direction ranging from 115 N to 350 N.

In the present application, the tensile breaking strength in the warp direction and in the weft direction is measured according to the following method: Tensile breaking strength and elongation at break: is measured according to ISO 13934-1: 2013 *"Textiles—Tensile properties of fabrics—Part 1: Determination of maximum force and elongation at maximum force using the strip method"*, 5 samples, width: 50 mm, Length: 200 mm between the jaws, Crosshead speed: 100 mm/min, Pre-load: 0.5 N, using a traction testing machine such as the Hounsfield model H5KS (Hounsfield, Redhill, England).

Such a tensile breaking strength in the warp direction and in the weft direction allows the transition part to complete adequately its function of support.

In embodiments, the third fabric shows a thickness ranging from 0.2 mm to 2.5 mm. Such a thickness allows the transition part to be less palpable under the skin, thereby conferring to the patient a natural feeling regarding the supported breast structure.

In embodiments, the yarns forming the third arrangement are monofilaments. Monofilaments allow obtaining a more natural appearance of the reconstructed breasts and also a more natural palpation feeling. Such monofilaments are less palpable and therefore confer a more natural feeling on the skin of the patient.

Elastic yarns may be used to provide the required elongation under 50N in the vertical direction for the third fabric. Alternatively or in combination, the weaving pattern or the knitting pattern may provide the required elongation under 50N in the vertical direction for the third fabric.

A first example of a porous knit suitable for forming a third fabric for the transition part of the prosthesis of the invention is a two-dimensional porous knit as described in WO2011/042811, namely obtained by knitting a monofilament of polyethylene terephthalate of diameter 0.08 mm on a warp knitting machine having two guide bars B1, B2, according to the following pattern, according to the ISO 11676 standard:

Bar B1: 1.0/1.2/1.0/2.3/2.1/2.3/4.5/4.3/4.5/3.2/3.4/3.2//
Bar B2: 4.5/4.3/4.5/3.2/3.4/3.2/1.0/1.2/1.0/2.3/2.1/2.3//

Guide bars B1 and B2 are threaded 1 full 1 empty and move symmetrically.

This knit will hereinafter be referred to as Knit A.

Another example of a porous knit suitable for forming a third fabric for the transition part of the prosthesis of the invention is a two-dimensional knit as described in U.S. Pat. No. 6,408,656, namely obtained by knitting a monofilament of polypropylene of diameter 0.10 mm on a warp knitting machine having two guide bars B1, B2, according to the following pattern, according to the ISO 11676 standard:

Bar B1: 5.4/4.3/2.1/0.1/1.2/3.4//
Bar B2: 0.1/1.2/3.4/5.4/4.3/2.1//

Guide bars B1 and B2 are threaded 1 full 1 empty and move symmetrically.

This knit will hereinafter be referred to as Knit B.

Another example of a porous knit suitable for forming a third fabric for the transition part of the prosthesis of the invention is a two-dimensional knit obtained by knitting a monofilament of polypropylene of diameter 0.12 mm knitted on a warp knitting machine having two guide bars B1, B2, the pattern followed being the following, according to the ISO 11676 standard:

Bar B1: 1.2/4.5/4.3/4.5/4.3/1.0/1.2/1.0//
Bar B2: 4.3/1.0/1.2/1.0/1.2/4.5/4.3/4.5//

Guide bars B1 and B2 are threaded 1 full 1 empty and move symmetrically.

This knit will hereinafter be referred to as Knit C.

The properties of Knits A, B and C measured according to the measuring methods described hereinabove are collected in the following table:

|  | Knit A | | Knit B | | Knit C | |
| --- | --- | --- | --- | --- | --- | --- |
|  | Warp | Weft | Warp | Weft | Warp | Weft |
| Tensile breaking strength (N) | 175 ± 12 | 129 ± 2 | 187 ± 16 | 149 ± 10 | 237 ± 6 | 201 ± 6 |
| Elongation under 50 N (%) | 54 ± 0 | 50 ± 6 | 43 ± 1 | 59 ± 1 | 38 ± 1 | 46 ± 0 |
| Thickness (mm) | 0.4 | | 0.4 | | 0.6 | |
| Pore size (mm) (width × height) | 1.5 × 1.5 | | 1.6 × 1.4 | | 2.0 × 2.4 | |

In embodiments, depending on which direction, warp or weft, may be selected to position Knit A as the third fabric of the prosthesis of the invention with respect to the vertical direction, E3 may either be 54% or 50%. In other embodiments, depending on which direction, warp or weft, may be selected to position Knit B as the third fabric of the prosthesis of the invention with respect to the vertical direction, E3 may either be 43% or 59%. In other embodiments, depending on which direction, warp or weft, may be selected to position Knit C as the third fabric of the prosthesis of the invention with respect to the vertical direction, E3 may either be 38% or 46%.

The reinforcement part is intended to receive the curve-shaped lower portion of a breast structure. In embodiments, the reinforcement part has a globally elongated shape in the horizontal direction, said shape showing a convex lower edge. Said shape may show a convex upper edge. Alternatively, said shape may show a concave upper edge.

The first fabric forming the reinforcement part of the prosthesis according to the invention may preferably have a generally elongate shape, for example oval or elliptic. The first fabric can have another initial shape and can then be cut to such an elongate shape, in particular to a shape adapted to the function of the reinforcement part. In particular, the shape of the first fabric of the prosthesis of the invention comprises a part capable of efficiently receiving the curved-shape lower portion of a breast structure. The first fabric is essentially delimited by a lower edge and an upper edge. The lower edge is preferably convex in order to optimize the conformity of the first fabric with the curved shape of the lower portion of the breast structure and the suturability of said first fabric to the chest wall. As such, the general shape of the lower edge is preferably convex.

In embodiments, the reinforcement part is provided with a reinforcement member configured for inducing a curved shape to said first fabric conformable with said curve-shaped lower portion of the breast structure. Such embodiments limit the risk of undesired pleating that may occur when implanting a textile over a rounded breast implant.

The reinforcement member may be a rigid or semi-rigid wire having a resiliency or elasticity allowing it to be deformed under the effect of a temporary stress. According to the present invention, the reinforcement member may have an initial curved state allowing the first fabric, and therefore the reinforcement part, to adopt a shape conformable to the curved shape of the lower portion of the breast structure.

The reinforcement member, such as a wire, of the prosthesis according to the invention may be substantially set back from the lower edge of the reinforcement part/first fabric.

The materials that may be suitable for producing the reinforcement member of the prosthesis according to the invention may be chosen from any biocompatible material having a certain rigidity and a certain resilience in order to meet the requirements described above.

In one embodiment, the reinforcement member, for example the wire, is made of a bioresorbable material. For example, the bioresorbable material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. For example, the bioresorbable material can be a copolymer of polylactic acid and of polyglycolic acid.

Alternatively, the reinforcement member of the prosthesis according to the invention is made of a non-bioresorbable material chosen from among polypropylenes, polyesters such as polyethyleneterephthalates, polyamides, silicones, polyether ether ketone (PEEK), polyether ketone ketone (PEKK), polyarylether ether ketone (PAEK), polyurethanes and mixtures thereof.

In another embodiment, said reinforcement member is formed by a combination of bioresorbable material and of non-bioresorbable material.

In one embodiment, the reinforcement member of the prosthesis according to the invention is an overmolded wire positioned in the area of a lower edge of said reinforcement part.

The reinforcement member may also be used to help suturing the reinforcement part to the chest wall or to the infra-mammary fold.

The transition part connects the reinforcement part to the fixation part. In embodiments, the transition part has substantially the shape of a portion of a circular crown. For example, a lower edge of said portion of a circular crown is also said upper edge of said shape of said reinforcement part.

In embodiments, the height h of the transition part ranges from 1 to 5 cm, preferably from 2 to 3 cm. Such embodiments allow providing to the entire prosthesis an elasticity and stretch allowing it to behave similarly to biological breast tissues, while not jeopardizing the tensile strength necessary to the prosthesis for performing its support function.

The fixation part is intended to be fixed to the pectoral muscle. In embodiments, said fixation part comprises a lower edge from which extend vertically and in the upper direction one or more arm(s) intended to be fixed to the pectoral muscle. Each arm having a lower end and an upper end, said lower end may be substantially larger in the horizontal direction than said upper end. Each arm may therefore have a substantially triangular shape. In embodiments, at least two said arms extend vertically and in the upper direction. For example, at least three said arms may extend vertically and in the upper direction. In embodiments, at least four said arms extend vertically and in the upper direction. For example, at least five said arms extend vertically and in the upper direction. In embodiments, at least six, seven or eight said arms extend vertically and in the upper direction.

The number of arm(s), their position and their shape allow inducing a conical shape to the fixation part. In particular, the surgeon does not need to cut the second fabric in order to arrange the fabric in a conical manner. Indeed, thanks to the lower end of each arm being substantially larger in the transverse direction than its upper end, the surgeon can easily form a conical mesh that conforms to the conical-like shape of the top of the breast structure.

In embodiments, said lower edge of said second fabric is also an upper edge of said portion of a circular crown.

In embodiments, the reinforcement part is linked to the transition part by means of sewing, gluing, welding, overmolding and combinations thereof. Alternatively, the reinforcement part and the transition part, and in particular the first fabric and the third fabric, may be made as a single structure. In embodiments, the transition part is linked to the fixation part by means of sewing, gluing welding, overmolding and combinations thereof. Alternatively, the transition part and the fixation part, and in particular the second fabric and the third fabric, may be made as a single structure.

Alternatively, the reinforcement part, the transition part and the fixation part, and in particular the first, second and third fabrics, are made as a single unitary structure. For example, using a knitting machine and the proper knitting pattern and/or yarn, the whole prosthesis, namely the reinforcement part, fixation part and transition part, and more particularly the first, second and third fabrics may be knitted and formed as a single unitary structure requiring no sewing or cutting. Such embodiment allows a very natural appearance as significant thickness variations or fabric ridges are thereby avoided.

In embodiments, a recess is provided in one or more of said reinforcement part, fixation part and transition part, said recess being intended to face the nipple-areola complex when the prosthesis is implanted. Such embodiments allow preserving the nipple-areola complex when a prosthesis of the invention is implanted in order to lift up breast tissue. Moreover, such embodiment allows facilitating the reconstruction of the nipple-areola complex further to the implantation of a breast implant and of the prosthesis of the invention. Indeed, the reconstruction of the nipple-areola complex usually takes place once the breast implant and the prosthesis of the invention are implanted and for example once cell colonization has already taken place. The presence of the recess in the prosthesis of the invention avoids an additional thickness in the area of the nipple-areola complex and leaves free said area. The surgeon does not have to take the prosthesis into account in this area when he proceeds to the reconstruction of the nipple-areola complex.

The prosthesis of the invention may be provided in a kit of prosthesis pieces, with each of the plurality of prosthesis pieces in the kit being of varying sizes (sizes may include small, medium, large, etc. . . . or may conform to well known bra sizes).

A second aspect of the present invention is a method for implanting a prosthesis of the invention for supporting a breast structure, such as a breast implant or breast tissue, comprising the following steps:

a) making an incision in the area of the infra-mammary fold, b) if a breast implant is needed, positioning said breast implant between the chest wall and the pectoral muscle after desinsertion of the pectoral muscle, c) positioning the prosthesis described above so that the curve-shaped lower portion of the breast structure is received in the reinforcement part, with a lower edge of the reinforcement part facing the chest wall, and an upper area of the fixation part facing the pectoral muscle, d) suturing the lower edge of the reinforcement part to the chest wall or to the infra-mammary fold, e) determining the best position of the fixation part with respect to said pectoral muscle, f) fixing the fixation part to the pectoral muscle, g) closing the incision.

For example, step e) may be completed by gripping and ungripping said fixation part as many times as necessary with the help of the barbs of said second fabric.

The method of the invention may be used in case of a reconstruction of a breast post mastectomy or for an oncoplastic surgery as a mastopexy post lumpectomy. The method of the invention may also be used for lifting up healthy breast tissue in pure aesthetic surgery.

BRIEF DESCRIPTION OF THE DRAWINGS

The prosthesis and method of the invention will now be further described in reference to the following description and attached drawings in which.

DETAILED DESCRIPTION OF THE EMBODIMENTS

Figure 1:
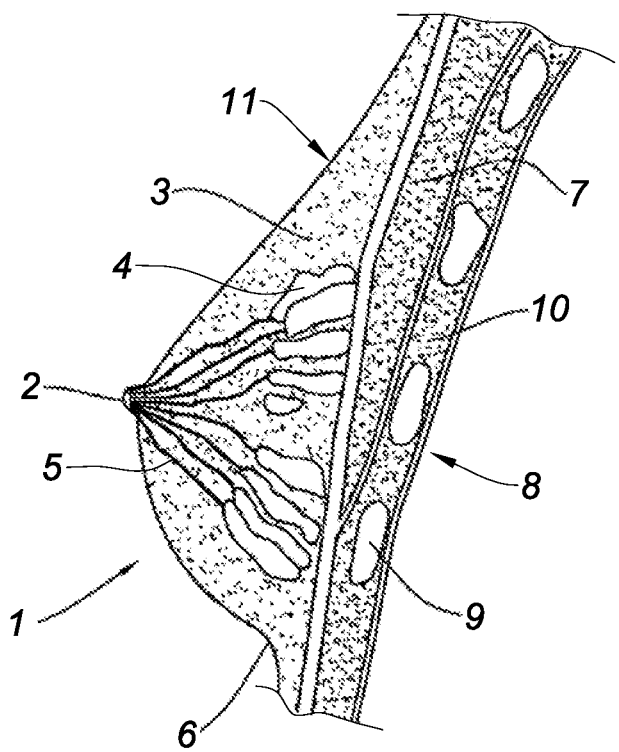
FIG. 1 is a side view of a healthy breast.
Figure 2:
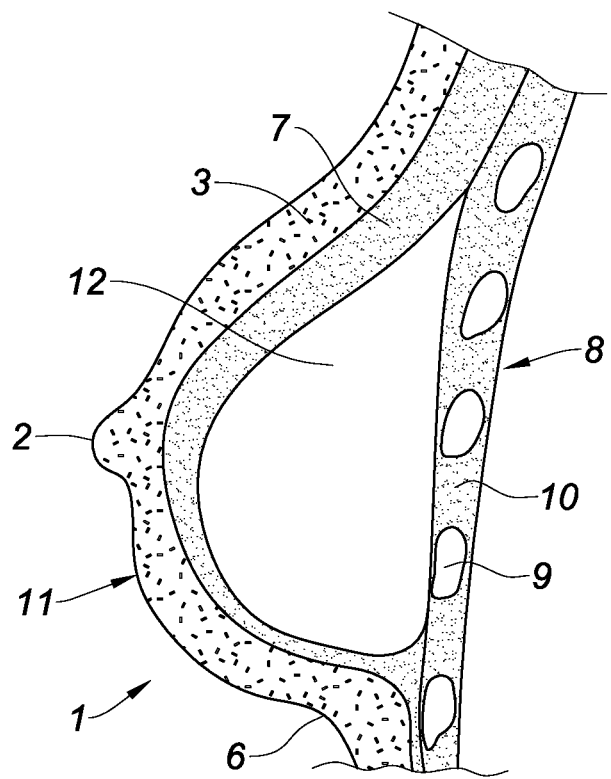
FIG. 2 is a side view of a reconstructed breast comprising a breast implant only.

With reference to FIGS. 3-8 are shown embodiments of a prosthesis 100 of the invention. As will appear from the description below, the prosthesis 100 is intended to be implanted into a female patient in a view of supporting a breast implant 12 (see FIG. 10) in breast reconstruction post mastectomy or in a view of supporting breast tissue (see FIGS. 11 and 12) in breast lifting aesthetics surgery.

With reference to FIGS. 3-8, the prosthesis 100 comprises three parts, a reinforcement part 101, a fixation part 102 and a transition part 103. The reinforcement part 101 is configured to receive at least a curve-shaped lower portion of a breast structure and is intended to be sutured to the chest wall or to the infra-mammary fold. The fixation part 102 is intended to be fixed to the pectoral muscle. The fixation part 102 will usually be surrounding the top conical portion of the breast structure (see FIGS. 10 and 11). The transition part 103 connects the reinforcement part 101 to the fixation part 102.

With reference to FIGS. 3-8 the reinforcement part 101 has a globally elongated shape in the horizontal direction, said shape showing a convex lower edge 104. The shape of the reinforcement part 101 is suited to engage over the lower or bottom curve portion of a breast structure in a manner to cup or otherwise support the structure in a bra-like fashion. The reinforcement part 101 will form the bottom part of the prosthesis and its lower edge is substantially an arch shaped perimeter edge, using a predetermined depth or arc corresponding to the natural shape of breast.

The convex lower edge 104 of the reinforcement part therefore allows encompassing the lower portion of a breast structure while remaining close to the chest wall or to the infra-mammary fold. As will appear later in the description, the lower edge 104 of the reinforcement part 101 is intended to be sutured or fixed to the chest wall or to the infra-mammary fold once the prosthesis 100 is implanted.

Figure 5:
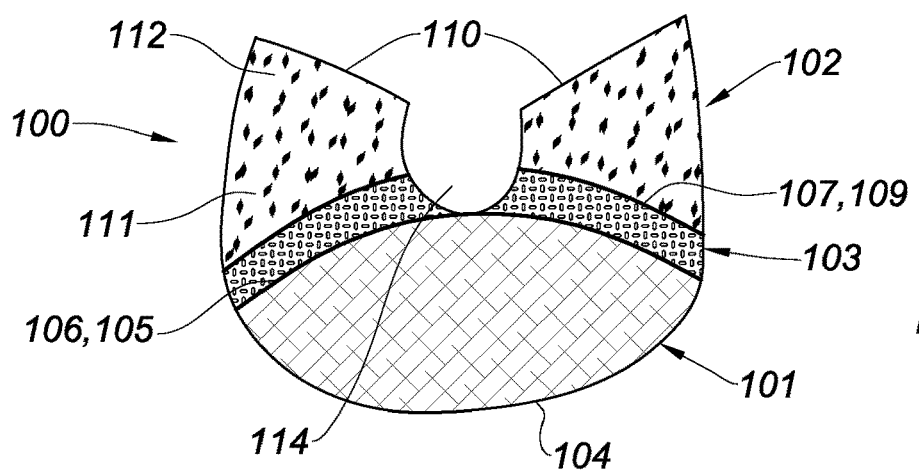
FIG. 5 is a front view of a third embodiment of a prosthesis according to the invention.
Figure 6:
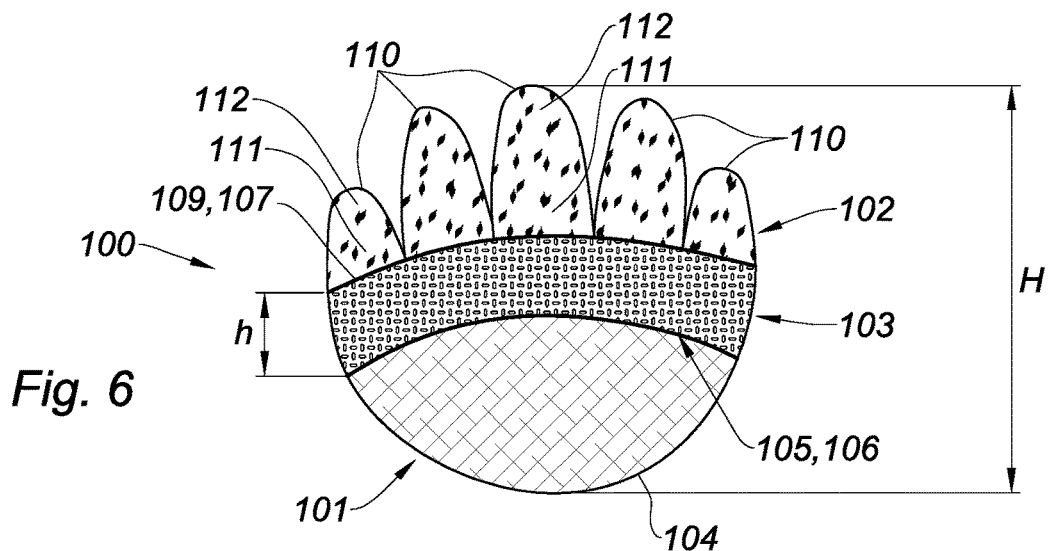
FIG. 6 is a front view of a fourth embodiment of a prosthesis according to the invention.
Figure 7:
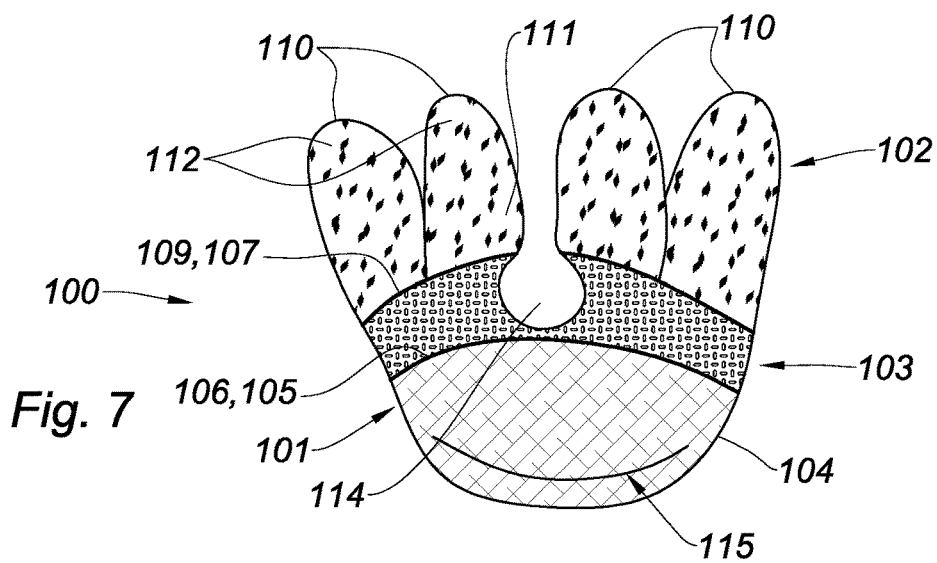
FIG. 7 is a front view of a fifth embodiment of a prosthesis according to the invention.

For example, the shape of the reinforcement part 101 may be generally oval or elliptical as shown on FIGS. 5-7. In such a case, the shape of the reinforcement part shows a convex upper edge 105.

Figure 3:
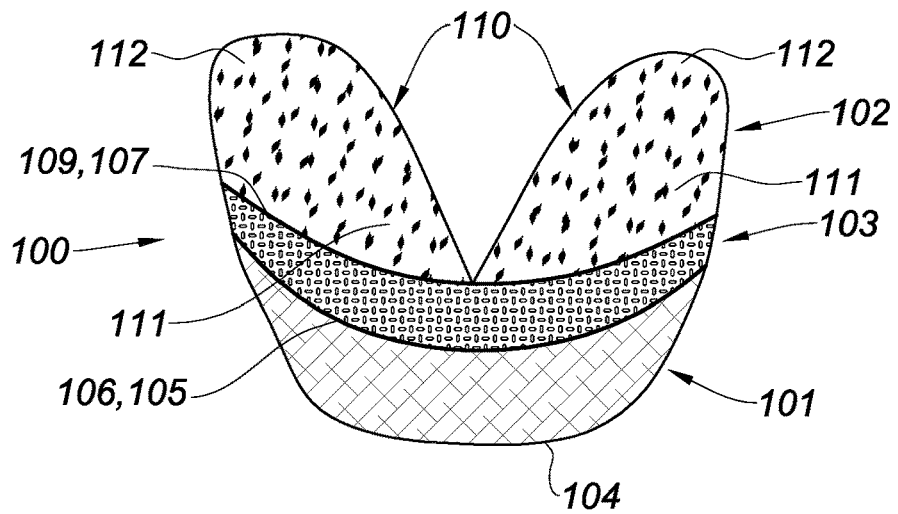
FIG. 3 is a front view of a first embodiment of a prosthesis according to the invention.
Figure 4:
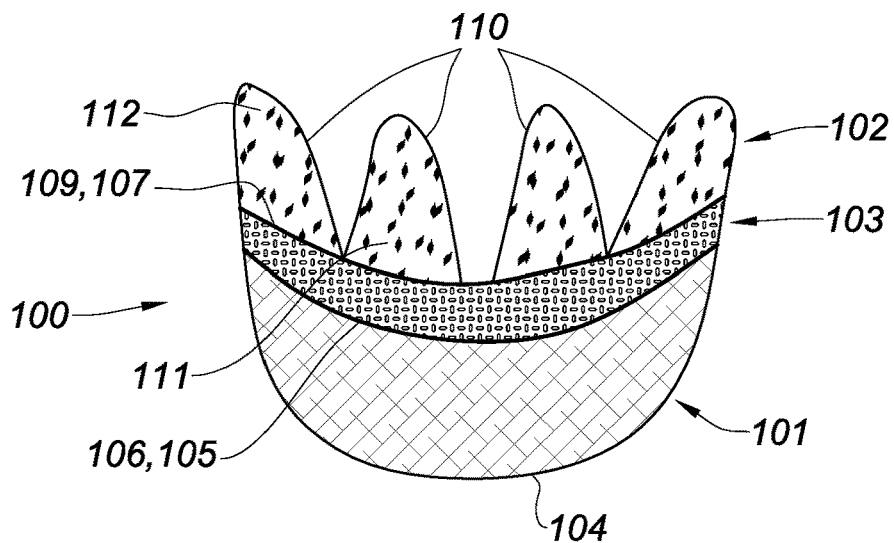
FIG. 4 is a front view of a second embodiment of a prosthesis according to the invention.
Figure 8:
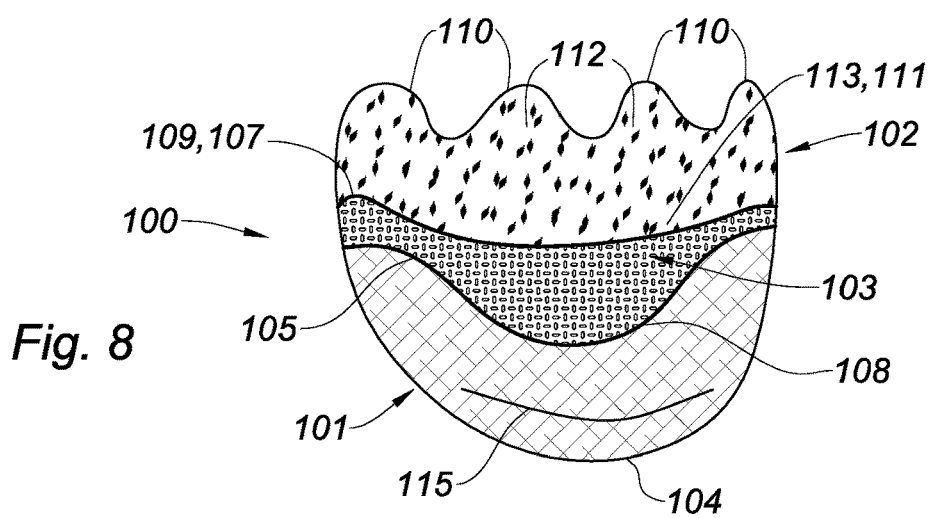
FIG. 8 is a front view of a sixth embodiment of a prosthesis according to the invention.

Alternatively, the shape of the reinforcement part 101 may show a concave upper edge 105, as shown on FIGS. 3, 4 and 8. For example, the reinforcement part 101 may have a crescent shape, as shown on FIGS. 3 and 4. With reference to FIG. 8, the concave upper edge 105 of the reinforcement part 101 may show an additional concave curve 108.

Figure 9:
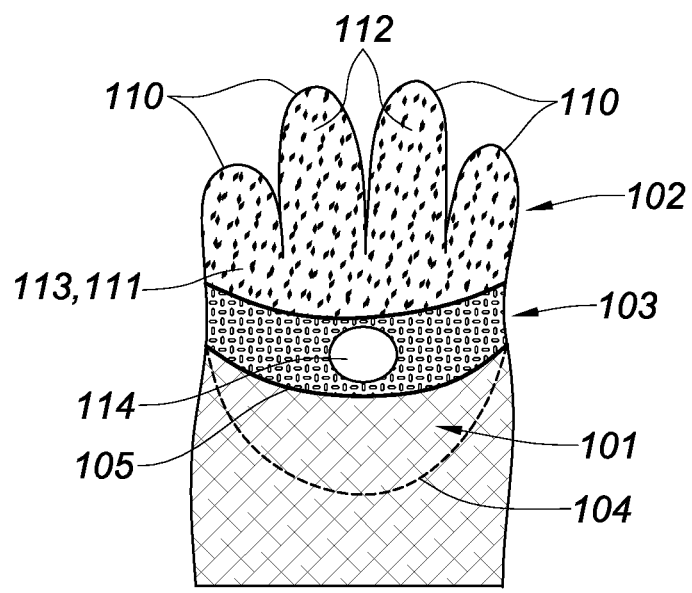
FIG. 9 is a front view of a seventh embodiment of a prosthesis according to the invention.

With reference to FIG. 9, the fabric used for forming the reinforcement part 101 may have another initial shape and can then be cut to such an elongate shape, in particular to a shape adapted to the function of the reinforcement part.

With reference to FIGS. 3-9, the transition part 103 connects the reinforcement part 101 to the fixation part 102. The transition part 103 may have substantially the shape of a portion of a circular crown. In particular, the transition part 103 shows a height h (see FIG. 6) in the vertical direction substantially constant. In this view, the lower edge 106 and the upper edge 107 of the transition part 103 are substantially parallel to each other.

Indeed, as will appear later in the description, the transition part 103 possesses an elongation greater than the elongation of the reinforcement part 101 and of the fixation part 102, so that stretch and elasticity close to the natural behavior of a healthy breast is conferred to the supported breast structure. In this view, having a substantially constant height h of the transition part 103 allows maintaining a relatively constant stretch feeling along the horizontal direction of the prosthesis 100, and therefore of the supported breast structure.

For example, the lower edge 106 of the portion of a circular crown forming the transition part 102 is also the upper edge 105 of the reinforcement part 101. With reference to FIGS. 3, 4, 8 and 9, the lower edge 106 and the upper edge 107 of the transition part 103 show therefore a concave shape. With reference to FIG. 8, the lower edge 106 and the upper edge 107 of the transition part 103 are not substantially parallel as the lower edge 106 of the transition part 103 comprises the concave curve 108, whereas the upper edge 107 does not include any additional curve.

On the contrary, with reference to FIGS. 5-7, the lower edge 106 and the upper edge 107 of the transition part 103 show therefore a convex shape.

In embodiments, H represents the total height of the prosthesis 100 and h the height of the transition part 103, along a vertical direction, when the prosthesis 100 is in a planar configuration, for example as shown on FIG. 6, the ratio h/H ranges from about 1/30 to about 1/2, preferably from about 1/12 to about 1/4.

In embodiments, the height h of the transition part ranges from 1 to 5 cm, preferably from 2 to 3 cm.

Such embodiments allow providing to the entire prosthesis an elasticity and stretch allowing it to behave similarly to biological breast tissues, while not jeopardizing the mechanical properties necessary for the prosthesis to perform its support function.

Figure 10:
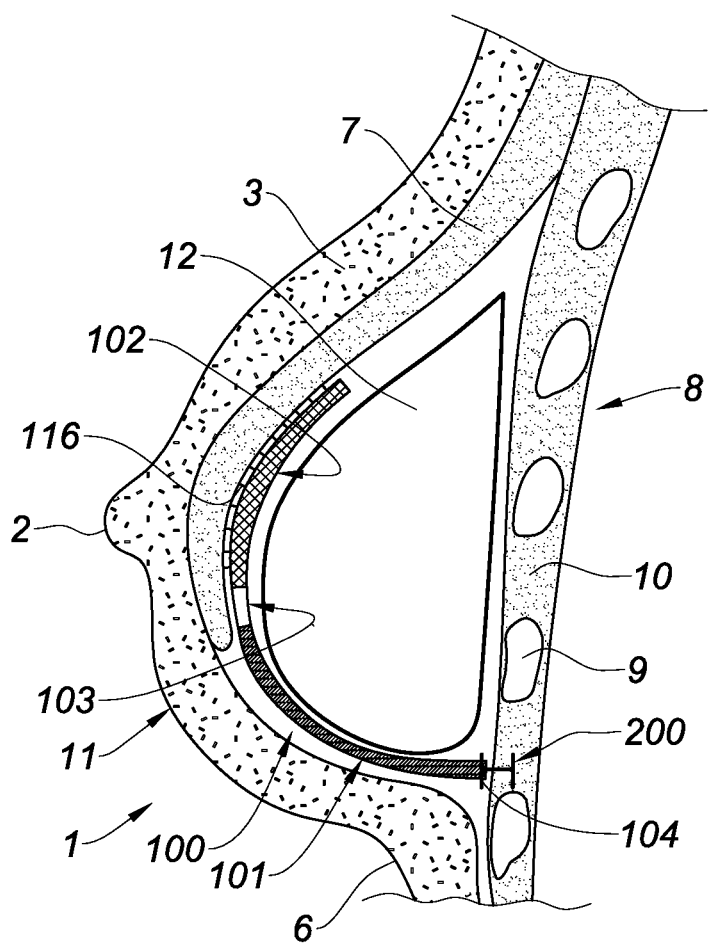
FIG. 10 is a side view of a prosthesis of FIGS. 3-9 implanted within a patient for supporting a breast implant.
Figure 11:
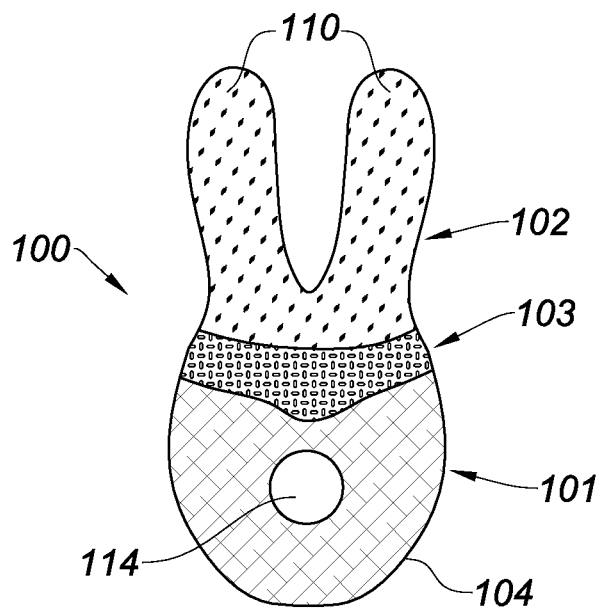
FIG. 11 is a front view of another embodiment of a prosthesis according to the invention.

The fixation part 102 forms the upper part of the prosthesis 100 and is intended to be fixed to the pectoral muscle once the prosthesis 100 is implanted (see FIGS. 10 and 11). The fixation part 102 may have any shape as long as said shape provides sufficient surface for overlapping an area of the pectoral muscle sufficient for ensuring a reliable fixation between the fixation part 102 and the pectoral muscle. For example, with reference to FIGS. 3-9, the fixation part 102 comprises a lower edge 109 from which extend vertically and in the upper direction one or more arm(s) 110 intended to be fixed to the pectoral muscle.

The arms 110 have a lower end 111 and an upper 112. Preferably, the lower 111 is larger in the horizontal direction than the upper 112, in order to ensure better resistance against gravity and better fixation. With reference to FIGS. 8 and 9, the lower ends 111 of the arms 110 form a continuous strip 113.

With reference to FIGS. 3 and 5, two arms 110 extend from the lower edge 109 of the fixation part 102 in the upper direction. With reference to FIGS. 4, 7 and 8, four arms 110 extend from the lower edge 109 of the fixation part 102 in the upper direction. With reference to FIGS. 6 and 9, five 110 extend from the lower edge 109 of the fixation part 102 in the upper direction.

The number of arms 110 may be varying from one up to ten, as long as said arms provide the necessary surface and strength for ensuring a reliable fixation to the pectoral muscle.

In addition, the shape and number of arms 110 allow shaping the fixation part 102 in a three-dimensional manner, in order to conform to the conical shape of the top portion of the breast structure. Thanks to the substantially triangular shape of the arms 110 and to their number preferably greater than one, pleats are avoided when the surgeon shapes the fixation part 102 in conformity with the three dimensional shape of the breast structure.

With reference to FIGS. 5, 7 and 9 is shown a recess 114 provided in the prosthesis. The recess 114 may be provided in the transition part 103 (see FIG. 9) or may be part of the fixation part 103 and of the transition part 102 as shown on FIGS. 5 and 7. The recess 114 is intended to face the nipple-areola complex when the prosthesis 100 is implanted. The presence of the recess 114 in the prosthesis 100 avoids an additional thickness in the area of the nipple-areola complex and leaves free this area when the surgeon proceeds to the reconstruction of nipple-areola complex if needed.

With reference to FIGS. 7 and 8 is shown a reinforcement member under the form of a wire 115, provided in the lower region of the reinforcement part 101. The wire 115 is configured for inducing a curved shape to the reinforcement part 101 conformable with the curve-shaped lower portion of the breast structure. The wire 115 is substantially set back from the lower edge of the reinforcement part 101.

The materials that may be suitable for producing the wire 115 may be chosen from any biocompatible material having a certain rigidity and a certain resilience in order to meet the requirements described above.

In one embodiment, the wire is made of a bioresorbable material. For example, the bioresorbable material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. For example, the bioresorbable material can be a copolymer of polylactic acid and of polyglycolic acid. Such embodiments allow avoiding that foreign material stay too long a time in the body of the patient.

Alternatively, the wire 115 may be made of a non-bioresorbable material chosen from among polypropylenes, polyesters such as polyethyleneterephthalates, polyamides, silicones, polyether ether ketone (PEEK), polyether ketone ketone (PEKK), polyarylether ether ketone (PAEK), polyurethanes and mixtures thereof. Additional support is therefore provided on a long term basis to the prosthesis 100 for holding the breast implant against gravity.

In another embodiment, said reinforcement member is formed by a combination of bioresorbable material and of non-bioresorbable material.

The wire 115 may be overmolded on the reinforcement part 101.

In embodiments, the reinforcement part 101 is linked to the transition part 103 by means of sewing, gluing, welding, overmolding and combinations thereof. In embodiments, the transition part 103 is linked to the fixation part 102 by means of sewing, gluing welding, overmolding and combinations thereof.

Alternatively, the first, second and third fabrics forming the reinforcement part, the transition part and the fixation part are made as a single unitary structure. For example, using a knitting machine and the proper knitting pattern and/or yarn, the whole prosthesis, namely the reinforcement part, fixation part and transition part, and more particularly the first, second and third fabrics may be knitted and formed as a single unitary structure requiring no sewing or cutting. Such embodiment allows a very natural appearance as significant thickness variations or fabric ridges are thereby avoided.

The reinforcement part 101 of FIGS. 3-9 comprises, or may consist in, a first fabric made of a first arrangement of yarns as described above in the present application, with in particular an elongation under 50N in the vertical direction referred to as E1. The fixation part 102 of FIGS. 3-9 comprises, or may consist in, a second fabric made of a second arrangement of yarns as described above in the present application, with in particular an elongation under 50N in the vertical direction referred to as E2. The transition part 103 of FIGS. 3-9 comprises, or may consist in, a third fabric made of a third arrangement of yarns as described above in the present application, with in particular an elongation under 50N in the vertical direction referred to as E3.

For each prosthesis 100 of FIGS. 3-9, the first, second and third fabrics are combined together so as to form the reinforcement part, the fixation part and the transition part, with the proviso that E3 is greater than E1 and greater than E2.

For example, for a prosthesis 100 of FIGS. 3-8, the reinforcement part 101 may be formed of Knit X described above, in combination with the fixation part 102 made of Knit F described above and with the transition part 103 made of Knit A described above. In such an embodiment, E1 is 25%, E2 is 5% and E3 is 50%.

In another example, for a prosthesis 100 of FIGS. 3-8, the reinforcement part 101 may be formed of Knit Y described above, in combination with the fixation part 102 made of Knit F described above and with the transition part 103 made of Knit B described above. In such an embodiment, E1 is 19%, E2 is 5% and E3 is 59%.

In another example, for a prosthesis 100 of FIGS. 3-8, the reinforcement part 101 may be formed of Knit Z described above, in combination with the fixation part 102 made of Knit F described above and with the transition part 103 made of Knit C described above. In such an embodiment, E1 is 35%, E2 is 5% and E3 is 46%.

With reference to FIG. 10 is shown a prosthesis 100 of FIGS. 3-9 in place within a patient in a view of supporting a breast implant 12. As shown on this Figure, the lower edge 104 of the reinforcement part 101 of the prosthesis 100 is sutured to the chest wall 8 by means of suture 200. Alternatively, the lower edge 104 of the reinforcement part 101 of the prosthesis 100 could be sutured to the infra-mammary fold 6. The reinforcement part 101 receives the lower curved portion of the breast implant 12 so as to cup said breast implant 12.

The fixation part 102 faces the pectoral muscle 7. In particular, in the surgical procedure shown, the implant breast 12 is positioned behind the pectoral muscle 7. The second fabric forming the fixation part 102 is provided with barbs 116 on its face fixed to the pectoral muscle 7.

With reference to FIG. 11 is shown another prosthesis 100 of the invention, comprising a reinforcement part 101, a fixation part 102 and a transition part 103. The fixation part 102 is provided with two arms 110. The prosthesis 100 is further provided with a recess 114 intended to face nipple-areola complex. In the prosthesis of FIG. 11, the recess 114 is located in the reinforcement part 101. Such a prosthesis is particularly adapted for lifting up healthy breast tissue in pure aesthetic surgery.

Figure 12:
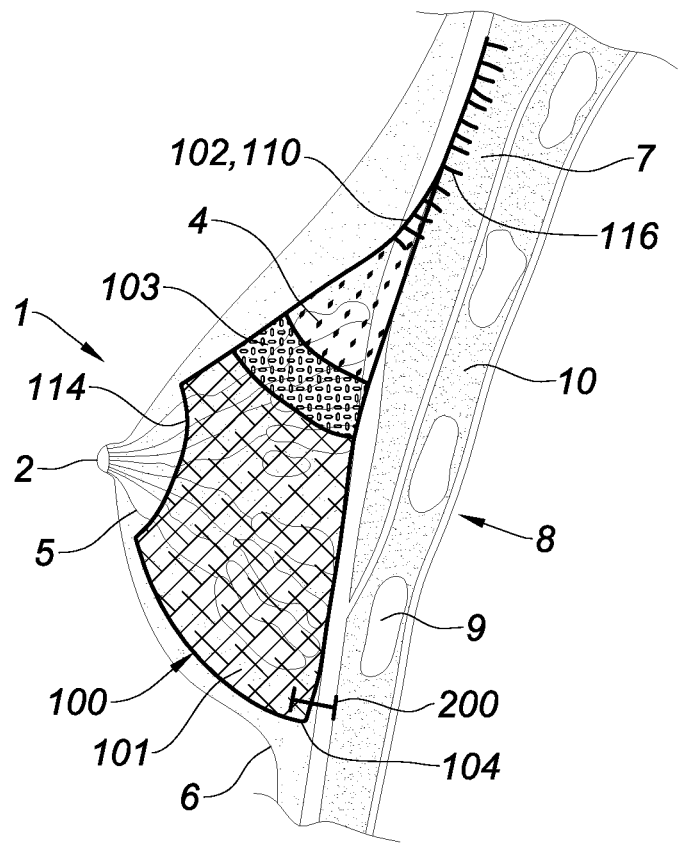
FIG. 12 is a side view of the prosthesis of FIG. 11 implanted within a patient for supporting breast tissue.

With reference to FIG. 12 is shown the prosthesis 100 of FIG. 11 in place within a patient in a view of supporting a healthy breast 1. No part of the healthy breast 1 has been removed and the lobules 4 and the milk ducts 5 are still present and received within the reinforcement part 101 of the prosthesis 100. As shown on this Figure, the lower edge 104 of the reinforcement part 101 of the prosthesis 100 is sutured to the chest wall 8 by means of suture 200. Alternatively, the lower edge 104 of the reinforcement part 101 of the prosthesis 100 could be sutured to the infra-mammary fold 6. The reinforcement part 101 receives the lower curved portion of the breast 1 so as to cup said breast 1.

The fixation part 102 faces the anterior face of the pectoral muscle 7. The second fabric forming the fixation part 102 is provided with barbs 116 on its face fixed to the anterior face of the pectoral muscle 7. The recess 114 is positioned facing the nipple-areola complex 2 so as to preserve it.

In order to implant the prosthesis 100 of the invention, the surgeon may perform the following steps:

a) making an incision in the area of the infra-mammary fold 6, b) if needed, for example in breast reconstruction surgery, positioning the breast implant 12 between the chest wall 8 and the pectoral muscle 7, c) positioning the prosthesis 100 so that the curve-shaped lower portion of the breast implant 12 or of the breast tissue is received in the reinforcement part 101, with the lower edge 104 of the reinforcement part 101 facing the chest wall 8, and an upper area of the fixation part 102 facing the pectoral muscle 7, d) suturing the lower edge 104 of the reinforcement part 101 to the chest wall 8, for example by means of suture 200, e) determining the best position of the fixation part 102 with respect to the pectoral muscle 8, f) fixing the fixation part 102 to the pectoral muscle 7, g) closing the incision.

For example, step e) may be completed by gripping and ungripping the fixation part 102, in particular the arms 110, as many times as necessary with the help of the barbs 116 present on the second fabric forming the fixation part 102. The barbs 116 may show a free end or head greater in width than a body of the barbs and a generally spheroidal or mushroom shape. The head of the barbs 116 are capable of penetrating in the pectoral muscle 7 for gripping each arm 110 to the pectoral muscle 7. The surgeon may examine whether the position of the arms 110 is correct or not. If the surgeon evaluates that the position should be corrected, he simply ungrips the arms 110 and proceeds to a second gripping of the arms 110 into the pectoral muscle 7. Thanks to the presence of the barbs 116, the fixation part 102 is repositionable. In addition, the determination of the adequate fixation position may be completed with the help of patient in a standing or seating position.

Because of its structure comprising at least three parts and because of the relative values of the respective elongations under 50N in the vertical direction of these three parts, the prosthesis of the invention once implanted in view of supporting a breast structure, allows for stretching and elasticity of the supported breast structure, in a manner very close to the natural behavior of a breast, thereby yielding a more natural appearance and movement during movement such as walking by the patient. The prosthesis of the invention further provides excellent support to the multi directional curves of the supported breast structure.

The structure of the prosthesis of the invention allows both efficient support to avoid sagging and bottoming out of the breast structure such as a breast implant and adequate elasticity for natural feel and movement. The prosthesis of the invention further supports the breast structure in the proper orientation.

What is claimed is:

1. A prosthesis for supporting a breast structure within a patient, the prosthesis comprising:

a reinforcement part comprising a first fabric made of a first arrangement of yarns and configured to receive at least a curve-shaped lower portion of a breast structure, said reinforcement part intended to be sutured to a chest wall or to an infra-mammary fold, said first arrangement of yarns conferring to said first fabric an elongation under 50N in a vertical direction of E1, a fixation part comprising a second fabric made of a second arrangement of yarns and intended to be fixed to a pectoral muscle, said second arrangement of yarns conferring to said second fabric an elongation under 50N in a vertical direction of E2, and a transition part comprising a third fabric made of a third arrangement of yarns, said transition part connecting together said reinforcement part and said fixation part, said third arrangement of yarns conferring to said third fabric an elongation under 50N in a vertical direction of E3, wherein E3 is more than 50% greater than E1.

2. The prosthesis of claim 1, wherein E3 is more than 100% greater than E1.

3. The prosthesis of claim 1, wherein E3 is more than 200% greater than E1.

4. The prosthesis of claim 1, wherein E3 and E1 are greater than E2.

5. The prosthesis of claim 1, wherein said prosthesis includes a total height H and said transition part has a height h, measured along the vertical direction, wherein said prosthesis in a planar configuration includes an h/H ratio ranging from about 1/30 to about 1/2.

6. The prosthesis of claim 5, wherein said h/H ratio ranges from about 1/12 to about 1/4.

7. The prosthesis of claim 1, wherein said reinforcement part has a globally elongated shape in a horizontal direction, said shape showing a convex lower edge.

8. The prosthesis of claim 1, wherein said transition part has substantially a shape of a portion of a circular crown.

9. The prosthesis of claim 1, wherein said fixation part comprises a lower edge from which extends vertically and in an upper direction one or more arms intended to be fixed to the pectoral muscle.

10. The prosthesis of claim 9, wherein the one or more arms each include a lower end and an upper end, said lower end is substantially larger in a horizontal direction than said upper end.

11. The prosthesis of claim 1, wherein said first fabric is a three-dimensional porous knit.

12. The prosthesis of claim 11, wherein said second and third fabrics are each two-dimensional porous knits.

13. The prosthesis of claim 11, wherein said three-dimensional porous knit includes pores having a size above 1 mm×1 mm.

14. The prosthesis of claim 1, wherein said first fabric shows a bursting strength above about 400 kPa.

15. The prosthesis of claim 1, wherein a face of said first fabric intended to be in contact with the breast structure is covered with a low friction coating.

16. The prosthesis of claim 1, wherein a face of said second fabric intended to face the pectoral muscle is provided with barbs protruding from said face of said second fabric, said barbs capable of fixing at least temporarily said face of said second fabric to the pectoral muscle.

17. The prosthesis of claim 1, wherein said reinforcement part is provided with a reinforcement member configured for inducing a curved shape to said first fabric conformable with said curve-shaped lower portion of the breast structure.

18. The prosthesis of claim 1, wherein said first, second and third fabrics are made as a single unitary structure.

19. The prosthesis of claim 1, wherein the prosthesis includes a recess in the transition part.

20. A prosthesis for supporting a breast structure within a patient, the prosthesis comprising:
    a reinforcement part comprising a first fabric made of a first arrangement of yarns and configured to receive at least a curve-shaped lower portion of a breast structure, said reinforcement part intended to be sutured to a chest wall or to an infra-mammary fold, said first arrangement of yarns conferring to said first fabric an elongation under 50N in a vertical direction of E1,
    a fixation part comprising a second fabric made of a second arrangement of yarns and intended to be fixed to a pectoral muscle, said second arrangement of yarns conferring to said second fabric an elongation under 50N in a vertical direction of E2, and
    a transition part comprising a third fabric made of a third arrangement of yarns, said transition part connecting together said reinforcement part and said fixation part, said third arrangement of yarns conferring to said third fabric an elongation under 50N in a vertical direction of E3,
    wherein E3 is more than 100% greater than E2.

* * * * *